(12) United States Patent
Andreas et al.

(10) Patent No.: US 7,553,324 B2
(45) Date of Patent: *Jun. 30, 2009

(54) FIXED STENT DELIVERY DEVICES AND METHODS

(75) Inventors: Bernard Andreas, Redwood City, CA (US); Jeffry J. Grainger, Portola Valley, CA (US)

(73) Assignee: Xtent, Inc., Menlo Park, CA (US)

( * ) Notice: Subject to any disclaimer, the term of this patent is extended or adjusted under 35 U.S.C. 154(b) by 590 days.

This patent is subject to a terminal disclaimer.

(21) Appl. No.: 10/686,025

(22) Filed: Oct. 14, 2003

(65) Prior Publication Data

US 2005/0080474 A1    Apr. 14, 2005

(51) Int. Cl.
*A61F 2/06* (2006.01)
(52) U.S. Cl. ..................................... 623/1.12
(58) Field of Classification Search ........... 623/1.11, 623/1.12, 1.15, 1.16, 1.2, 1.23; 606/191, 606/192, 194, 198
See application file for complete search history.

(56) References Cited

U.S. PATENT DOCUMENTS

| | | | |
|---|---|---|---|
| 4,069,825 | A | 1/1978 | Akiyama |
| 4,468,224 | A | 8/1984 | Enzmann et al. |
| 4,512,338 | A | 4/1985 | Balko |
| 4,564,014 | A | 1/1986 | Fogarty et al. |
| 4,580,568 | A | 4/1986 | Gianturco |
| 4,681,110 | A | 7/1987 | Wiktor |
| 4,733,665 | A | 3/1988 | Palmaz |
| 4,739,762 | A | 4/1988 | Palmz |
| 4,762,129 | A | 8/1988 | Bonzel |
| 4,775,337 | A | 10/1988 | Van Wagener et al. |
| 4,776,337 | A | 10/1988 | Palmaz |
| 4,886,062 | A | 12/1989 | Wiktor |

(Continued)

FOREIGN PATENT DOCUMENTS

EP            203945 B2     12/1986

(Continued)

OTHER PUBLICATIONS

Colombo, "The Invatec Bifurcation Stent Solution" Bifurcation Stents: Novel Solutions, TCT 2003, Washington: Sep. 15-19, 2003, 24 pages total.

(Continued)

*Primary Examiner*—Kevin T Truong
(74) *Attorney, Agent, or Firm*—Townsend and Townsend and Crew LLP; Jeff Grainger

(57) ABSTRACT

Stent delivery devices and methods include multiple stents or stent segments mounted at fixed positions on an expandable member of the stent delivery catheter. One or more of the fixed-position stents may be selectively deployed in a body lumen such as a blood vessel by positioning one or more sheaths to constrain some stents while exposing other for deployment. Some embodiments include two axially movable sheaths for serially deploying stents while containing a portion of the expandable balloon from which stents have been deployed. Other embodiments include inner and outer balloon shafts to allow the balloon to be retracted into the delivery catheter as stents are deployed. Devices and methods of the invention provide enhanced serial deployment of multiple stents or stent segments while reducing the risk of damage to an expandable deployment member.

13 Claims, 8 Drawing Sheets

U.S. PATENT DOCUMENTS

| | | | |
|---|---|---|---|
| 4,988,356 A | 1/1991 | Crittenden et al. | |
| 4,994,066 A | 2/1991 | Voss | |
| 4,994,069 A | 2/1991 | Ritchart et al. | |
| 5,013,318 A | 5/1991 | Spranza, III | |
| 5,040,548 A | 8/1991 | Yock | |
| 5,064,435 A | 11/1991 | Porter | |
| 5,092,877 A | 3/1992 | Pinchuk | |
| 5,102,417 A | 4/1992 | Palmz | |
| 5,104,404 A | 4/1992 | Wolff | |
| 5,135,535 A | 8/1992 | Kramer | |
| 5,195,984 A | 3/1993 | Schatz | |
| 5,201,757 A * | 4/1993 | Heyn et al. | 606/198 |
| 5,217,495 A | 6/1993 | Kaplan et al. | |
| 5,226,913 A | 7/1993 | Pinchuk | |
| 5,246,421 A | 9/1993 | Saab | |
| 5,273,536 A | 12/1993 | Savas | |
| 5,282,824 A | 2/1994 | Gianturco | |
| 5,300,085 A | 4/1994 | Yock | |
| 5,312,415 A | 5/1994 | Palermo | |
| 5,334,187 A | 8/1994 | Fischell et al. | |
| 5,421,955 A | 6/1995 | Lau et al. | |
| 5,458,615 A | 10/1995 | Klemm et al. | |
| 5,478,349 A | 12/1995 | Nicholas | |
| 5,490,837 A | 2/1996 | Blaeser et al. | |
| 5,496,346 A | 3/1996 | Horzewski et al. | |
| 5,501,227 A | 3/1996 | Yock | |
| 5,507,768 A | 4/1996 | Lau et al. | |
| 5,507,771 A | 4/1996 | Gianturco | |
| 5,514,093 A | 5/1996 | Ellis et al. | |
| 5,514,154 A | 5/1996 | Lau et al. | |
| 5,527,354 A | 6/1996 | Fontaine et al. | |
| 5,549,551 A | 8/1996 | Peacock, III et al. | |
| 5,549,563 A | 8/1996 | Kronner | |
| 5,549,635 A | 8/1996 | Solar | |
| 5,554,181 A | 9/1996 | Das | |
| 5,562,725 A | 10/1996 | Schmitt et al. | |
| 5,571,086 A | 11/1996 | Kaplan et al. | |
| 5,593,412 A | 1/1997 | Martinez et al. | |
| 5,607,444 A | 3/1997 | Lam | |
| 5,607,463 A | 3/1997 | Schwartz et al. | |
| 5,628,775 A | 5/1997 | Jackson et al. | |
| 5,634,928 A | 6/1997 | Fischell et al. | |
| 5,662,675 A | 9/1997 | Polanskyj Stockert et al. | |
| 5,676,654 A | 10/1997 | Ellis et al. | |
| 5,683,451 A | 11/1997 | Lenker et al. | |
| 5,697,948 A | 12/1997 | Marin et al. | |
| 5,702,418 A | 12/1997 | Ravenscroft | |
| 5,709,701 A * | 1/1998 | Parodi | 606/194 |
| 5,722,669 A | 3/1998 | Shimizu et al. | |
| 5,723,003 A | 3/1998 | Winston et al. | |
| 5,735,869 A | 4/1998 | Fernandez-Aceytuno | |
| 5,749,848 A | 5/1998 | Jang et al. | |
| 5,749,921 A | 5/1998 | Lenker et al. | |
| 5,755,772 A | 5/1998 | Evans et al. | |
| 5,755,776 A | 5/1998 | Al-Saadon | |
| 5,755,781 A | 5/1998 | Jayaraman | |
| 5,769,882 A | 6/1998 | Fogarty et al. | |
| 5,772,669 A | 6/1998 | Vrba | |
| 5,776,141 A | 7/1998 | Klein et al. | |
| 5,800,519 A | 9/1998 | Sandock | |
| 5,807,398 A | 9/1998 | Shaknovich | |
| 5,824,040 A | 10/1998 | Cox et al. | |
| 5,824,041 A | 10/1998 | Lenker et al. | |
| 5,836,964 A | 11/1998 | Richter et al. | |
| 5,843,092 A | 12/1998 | Heller et al. | |
| 5,858,556 A | 1/1999 | Eckert et al. | |
| 5,870,381 A | 2/1999 | Kawasaki et al. | |
| 5,879,370 A | 3/1999 | Fischell et al. | |
| 5,891,190 A | 4/1999 | Boneau | |
| 5,895,398 A | 4/1999 | Wensel et al. | |
| 5,899,935 A | 5/1999 | Ding | |
| 5,902,332 A | 5/1999 | Schatz | |
| 5,919,175 A | 7/1999 | Sirhan | |
| 5,922,020 A | 7/1999 | Klein et al. | |
| 5,961,536 A | 10/1999 | Mickley et al. | |
| 5,968,069 A | 10/1999 | Dusbabek et al. | |
| 5,976,107 A | 11/1999 | Mertens et al. | |
| 5,976,155 A | 11/1999 | Foreman et al. | |
| 5,980,484 A | 11/1999 | Ressemann et al. | |
| 5,980,486 A | 11/1999 | Enger | |
| 5,980,514 A | 11/1999 | Kupiecki et al. | |
| 5,980,552 A | 11/1999 | Pinchasik et al. | |
| 5,984,957 A | 11/1999 | Laptewicz, Jr. et al. | |
| 5,997,563 A | 12/1999 | Kretzers et al. | |
| 6,007,517 A | 12/1999 | Anderson | |
| 6,022,359 A | 2/2000 | Frantzen | |
| 6,033,434 A | 3/2000 | Borghi | |
| 6,039,721 A | 3/2000 | Johnson et al. | |
| 6,042,589 A | 3/2000 | Marianne | |
| 6,056,722 A | 5/2000 | Jayaraman | |
| 6,066,155 A | 5/2000 | Amann et al. | |
| 6,068,655 A | 5/2000 | Seguin et al. | |
| 6,090,063 A | 7/2000 | Makower | |
| 6,090,136 A * | 7/2000 | McDonald et al. | 623/1.23 |
| 6,102,942 A | 8/2000 | Ahari | |
| 6,106,530 A | 8/2000 | Harada | |
| RE36,857 E | 9/2000 | Euteneuer et al. | |
| 6,120,522 A | 9/2000 | Vrba et al. | |
| 6,123,712 A | 9/2000 | Di Caprio et al. | |
| 6,123,723 A | 9/2000 | Konya et al. | |
| 6,126,685 A | 10/2000 | Lenker et al. | |
| 6,129,756 A | 10/2000 | Kugler | |
| 6,143,016 A | 11/2000 | Bleam et al. | |
| 6,165,167 A | 12/2000 | Delaloye | |
| 6,179,878 B1 | 1/2001 | Duering | |
| 6,187,034 B1 | 2/2001 | Frantzen | |
| 6,190,402 B1 | 2/2001 | Horton et al. | |
| 6,196,995 B1 | 3/2001 | Fagan | |
| 6,200,337 B1 | 3/2001 | Moriuchi et al. | |
| 6,241,691 B1 | 6/2001 | Ferrera et al. | |
| 6,251,132 B1 | 6/2001 | Ravenscroft et al. | |
| 6,251,134 B1 | 6/2001 | Alt et al. | |
| 6,254,612 B1 | 7/2001 | Hieshima | |
| 6,254,628 B1 | 7/2001 | Wallace et al. | |
| 6,258,117 B1 | 7/2001 | Camrud et al. | |
| 6,267,783 B1 | 7/2001 | Letendre et al. | |
| 6,273,895 B1 | 8/2001 | Pinchuk et al. | |
| 6,273,913 B1 | 8/2001 | Wright et al. | |
| 6,312,458 B1 | 11/2001 | Golds | |
| 6,315,794 B1 | 11/2001 | Richter | |
| 6,319,277 B1 | 11/2001 | Rudnick et al. | |
| 6,325,823 B1 | 12/2001 | Horzewski et al. | |
| 6,357,104 B1 | 3/2002 | Myers | |
| 6,375,676 B1 | 4/2002 | Cox | |
| 6,383,171 B1 | 5/2002 | Gifford et al. | |
| 6,409,753 B1 | 6/2002 | Brown et al. | |
| 6,415,696 B1 | 7/2002 | Erickeson et al. | |
| 6,419,693 B1 | 7/2002 | Fariabi | |
| 6,451,025 B1 | 9/2002 | Jervis | |
| 6,451,050 B1 | 9/2002 | Rudakov et al. | |
| 6,468,298 B1 | 10/2002 | Pelton | |
| 6,468,299 B2 | 10/2002 | Stack et al. | |
| 6,485,510 B1 | 11/2002 | Camrud et al. | |
| 6,488,694 B1 | 12/2002 | Lau et al. | |
| 6,488,702 B1 | 12/2002 | Besselink | |
| 6,511,468 B1 | 1/2003 | Gragg et al. | |
| 6,520,987 B1 | 2/2003 | Plante | |
| 6,527,789 B1 | 3/2003 | Lau et al. | |
| 6,527,799 B2 | 3/2003 | Shanley | |
| 6,555,157 B1 | 4/2003 | Hossainy | |
| 6,575,993 B1 | 6/2003 | Yock | |
| 6,582,394 B1 | 6/2003 | Reiss et al. | |
| 6,585,756 B1 | 7/2003 | Strecker | |
| 6,592,549 B2 | 7/2003 | Gerdts et al. | |

| | | |
|---|---|---|
| 6,599,296 B1 | 7/2003 | Gillick et al. |
| 6,602,282 B1 | 8/2003 | Yan |
| 6,605,062 B1 | 8/2003 | Hurley et al. |
| 6,645,547 B1 | 11/2003 | Shekalim et al. |
| 6,656,212 B2 | 12/2003 | Ravenscroft et al. |
| 6,666,883 B1 | 12/2003 | Seguin et al. |
| 6,676,695 B2 | 1/2004 | Solem |
| 6,679,909 B2 | 1/2004 | McIntosh et al. |
| 6,692,465 B2 | 2/2004 | Kramer |
| 6,699,280 B2 | 3/2004 | Camrud et al. |
| 6,702,843 B1 | 3/2004 | Brown |
| 6,709,379 B1 | 3/2004 | Brandau et al. |
| 6,712,827 B2 | 3/2004 | Ellis et al. |
| 6,712,845 B2 | 3/2004 | Hossainy |
| 6,723,071 B2 | 4/2004 | Gerdts et al. |
| 6,743,251 B1 | 6/2004 | Eder |
| 6,800,065 B2 | 10/2004 | Duane et al. |
| 6,837,901 B2 | 1/2005 | Rabkin et al. |
| 6,849,084 B2 * | 2/2005 | Rabkin et al. ............... 623/1.12 |
| 7,137,993 B2 | 11/2006 | Acosta et al. |
| 7,147,656 B2 | 12/2006 | Andreas et al. |
| 7,192,440 B2 | 3/2007 | Andreas et al. |
| 2001/0020154 A1 | 9/2001 | Bigus et al. |
| 2001/0020181 A1 | 9/2001 | Layne |
| 2001/0044595 A1 | 11/2001 | Reydel et al. |
| 2002/0037358 A1 | 3/2002 | Barry et al. |
| 2002/0107560 A1 | 8/2002 | Richter |
| 2002/0111671 A1 | 8/2002 | Stenzel |
| 2002/0128706 A1 | 9/2002 | Ospyka |
| 2002/0138132 A1 | 9/2002 | Brown |
| 2002/0151924 A1 | 10/2002 | Shiber |
| 2002/0151955 A1 | 10/2002 | Tran et al. |
| 2002/0156496 A1 | 10/2002 | Chermoni |
| 2002/0177890 A1 | 11/2002 | Lenker |
| 2002/0188343 A1 | 12/2002 | Mathis |
| 2002/0188347 A1 | 12/2002 | Mathis |
| 2002/0193873 A1 | 12/2002 | Brucker et al. |
| 2003/0045923 A1 | 3/2003 | Bashiri et al. |
| 2003/0093143 A1 | 5/2003 | Zhao et al. |
| 2003/0097169 A1 | 5/2003 | Brucker et al. |
| 2003/0114912 A1 | 6/2003 | Sequin et al. |
| 2003/0114919 A1 | 6/2003 | McQuiston et al. |
| 2003/0114922 A1 | 6/2003 | Iwasaka et al. |
| 2003/0125791 A1 | 7/2003 | Sequin et al. |
| 2003/0125800 A1 | 7/2003 | Shulze et al. |
| 2003/0135266 A1 | 7/2003 | Chew et al. |
| 2003/0139796 A1 | 7/2003 | Sequin et al. |
| 2003/0139797 A1 | 7/2003 | Johnson et al. |
| 2003/0139798 A1 | 7/2003 | Brown et al. |
| 2003/0176909 A1 | 9/2003 | Kusleika |
| 2003/0191516 A1 | 10/2003 | Weldon et al. |
| 2003/0195609 A1 | 10/2003 | Berenstein |
| 2003/0199821 A1 | 10/2003 | Gerdts et al. |
| 2003/0204238 A1 | 10/2003 | Tedeschi |
| 2003/0225446 A1 | 12/2003 | Hartley |
| 2004/0024450 A1 | 2/2004 | Shulze et al. |
| 2004/0030380 A1 | 2/2004 | Shulze et al. |
| 2004/0087965 A1 | 5/2004 | Levine et al. |
| 2004/0093061 A1 | 5/2004 | Acosta et al. |
| 2004/0093067 A1 | 5/2004 | Israel |
| 2004/0093077 A1 | 5/2004 | White et al. |
| 2004/0098081 A1 | 5/2004 | Landreville et al. |
| 2004/0117008 A1 | 6/2004 | Wnendt et al. |
| 2004/0186551 A1 | 9/2004 | Kao et al. |
| 2004/0193245 A1 | 9/2004 | Deem et al. |
| 2004/0215165 A1 | 10/2004 | Coyle et al. |
| 2004/0215312 A1 | 10/2004 | Andreas |
| 2004/0249435 A1 | 12/2004 | Andreas et al. |
| 2005/0010276 A1 | 1/2005 | Acosta et al. |
| 2005/0038505 A1 | 2/2005 | Shuize et al. |
| 2005/0101624 A1 | 5/2005 | Betts et al. |
| 2005/0125051 A1 | 6/2005 | Eidenschink et al. |
| 2005/0131008 A1 | 6/2005 | Betts et al. |
| 2005/0133164 A1 | 6/2005 | Andreas et al. |
| 2005/0143827 A1 | 6/2005 | Globerman et al. |
| 2005/0149159 A1 | 7/2005 | Andreas et al. |
| 2005/0209674 A1 | 9/2005 | Kutscher et al. |
| 2005/0222671 A1 | 10/2005 | Schaeffer et al. |
| 2005/0288763 A1 | 12/2005 | Andreas et al. |
| 2006/0229700 A1 | 10/2006 | Acosta et al. |
| 2006/0229706 A1 | 10/2006 | Shulze et al. |
| 2006/0282147 A1 | 12/2006 | Andreas et al. |
| 2006/0282150 A1 | 12/2006 | Olson et al. |

FOREIGN PATENT DOCUMENTS

| | | |
|---|---|---|
| EP | 274129 B1 | 7/1988 |
| EP | 282143 | 9/1988 |
| EP | 0 505 686 | 9/1992 |
| EP | 0 533 960 | 3/1993 |
| EP | 0 714 640 | 6/1996 |
| EP | 0 596 145 | 5/1997 |
| EP | 947180 | 10/1999 |
| EP | 1523959 A2 | 4/2005 |
| EP | 1523960 A2 | 4/2005 |
| EP | 1266638 B1 | 10/2005 |
| WO | WO 96/33677 | 10/1996 |
| WO | WO 97/46174 | 12/1997 |
| WO | WO 97/48351 | 12/1997 |
| WO | WO 99/01087 A1 | 1/1999 |
| WO | WO 00/12832 A3 | 3/2000 |
| WO | WO 00/15151 A1 | 3/2000 |
| WO | WO 00/32136 A1 | 6/2000 |
| WO | WO 00/41649 A1 | 7/2000 |
| WO | WO 00/50116 | 8/2000 |
| WO | WO 00/62708 | 10/2000 |
| WO | WO 00/72780 | 12/2000 |
| WO | WO 01/70297 | 9/2001 |
| WO | WO 01/91918 | 12/2001 |
| WO | WO 03/022178 A1 | 3/2003 |
| WO | WO 03/047651 | 6/2003 |
| WO | WO 03/051425 A2 | 6/2003 |
| WO | WO 03/075797 | 9/2003 |
| WO | WO 2004/017865 | 3/2004 |
| WO | WO 2004/043299 | 5/2004 |
| WO | WO 2004/043301 | 5/2004 |
| WO | WO 2004/043510 | 5/2004 |
| WO | WO 2004/052237 | 6/2004 |

OTHER PUBLICATIONS

Cooley et al., "Applications of Ink-Jet Printing Technology to BioMEMs and Microfluidic Systems," Proceedings, SPIE Conference on Microfluidics and BioMEMs, (Oct. 2001).

Lefevre et al. "Approach to Coronary Bifurcation Stenting in 2003," Euro PCR, (May 2003) 28 pages total.

"Stent". Definitions from Dictionary.com. Unabridged 9v1.01). Retrieved Sep. 22, 2006, from Dictionary.com website: <http://dictionary.reference.com/search?q=stent>.

Stimpson et al., Parallel Production of Oligonucleotide Arrays Using Membranes and Reagent Jet Printing, BioTechniques 25:886-890 (Nov. 1998).

Evans Analytical Group, "Functional Sites on Non-polymeric Materials: Gas Plasma Treatment and Surface Analysis," http://www.eaglabs.com.

Joung et al., "Estrogen Release from Metallic Stent Surface for the Prevention of Restenosis," Journal of Controlled Release 92 (2003) pp. 83-91.

* cited by examiner

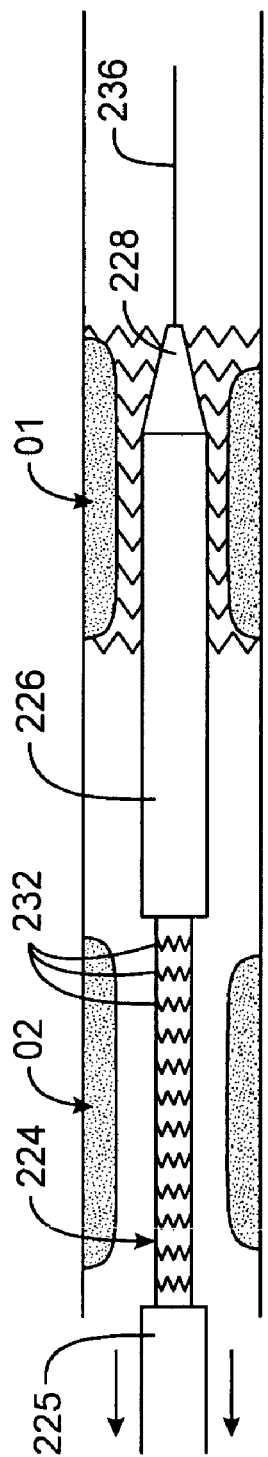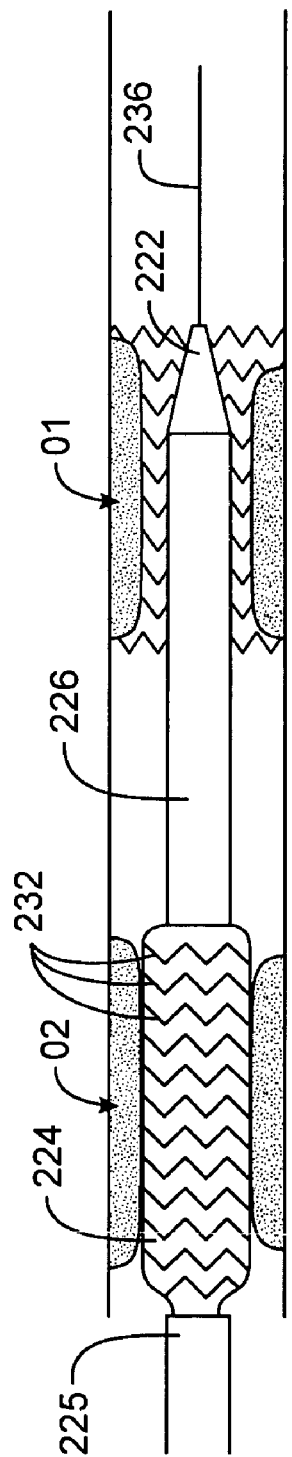
FIG. 3E
FIG. 3F

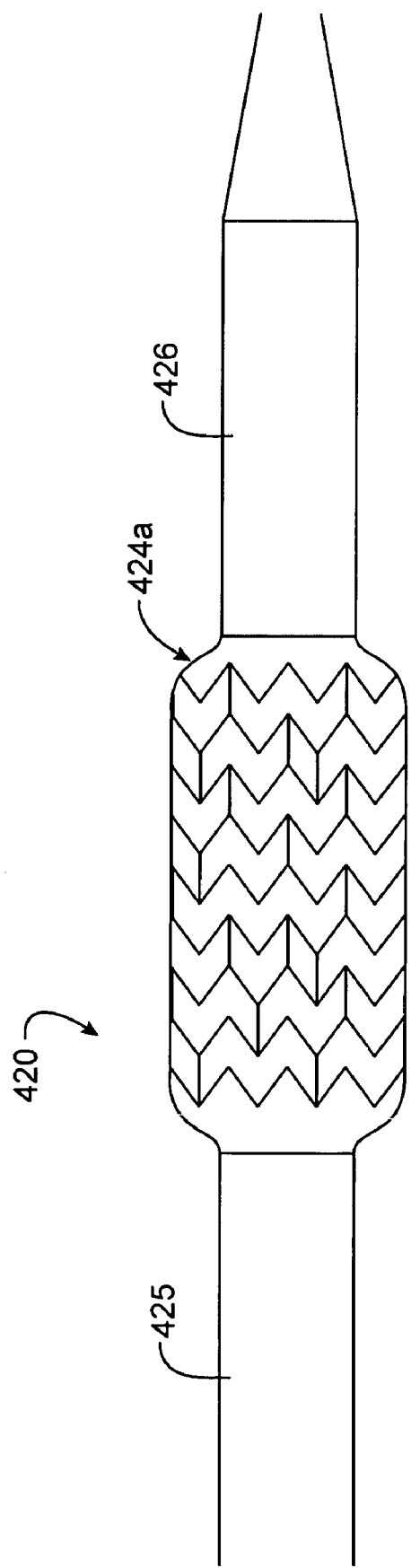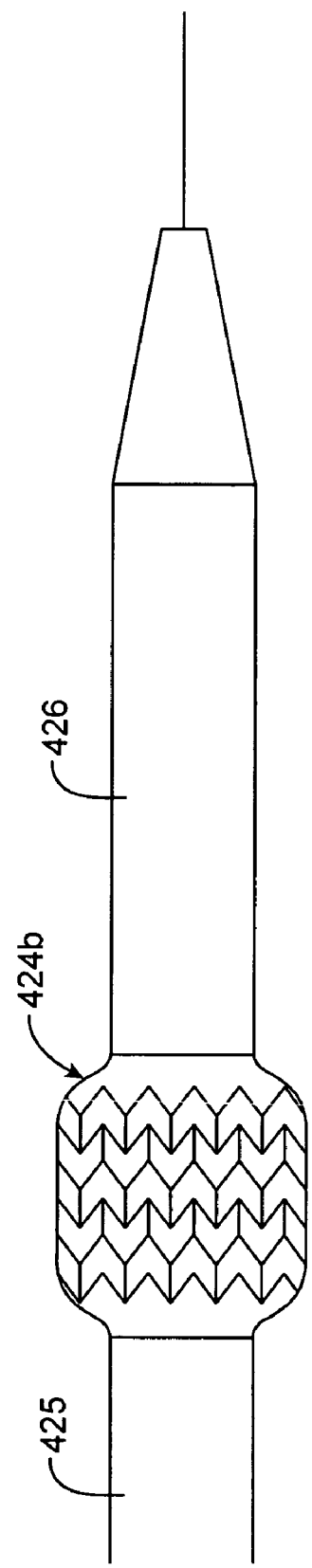
FIG. 5A
FIG. 5B

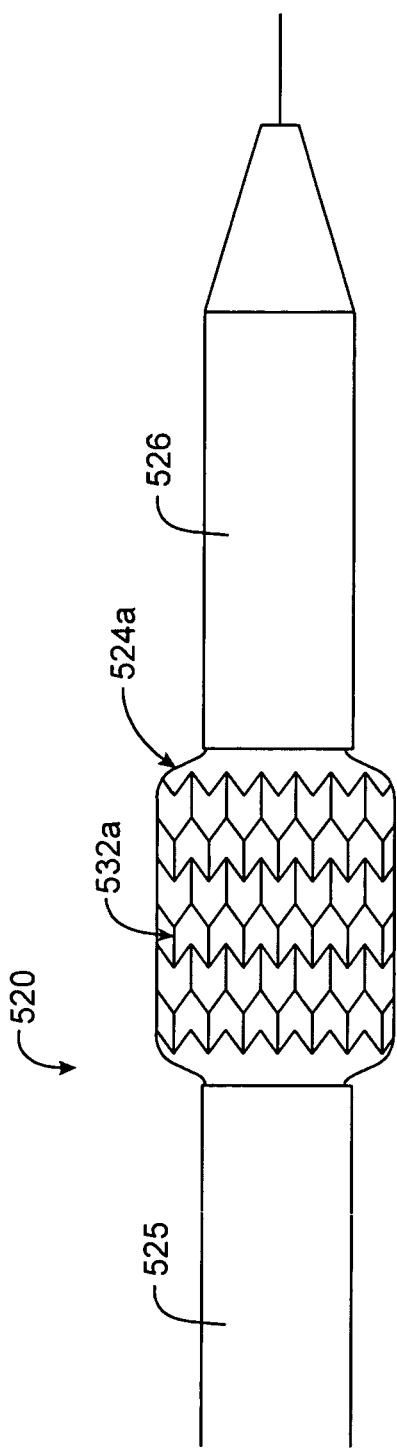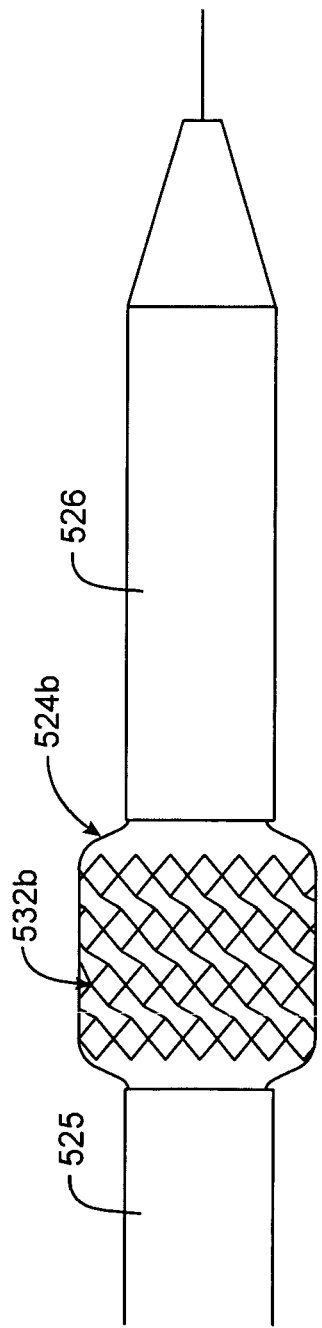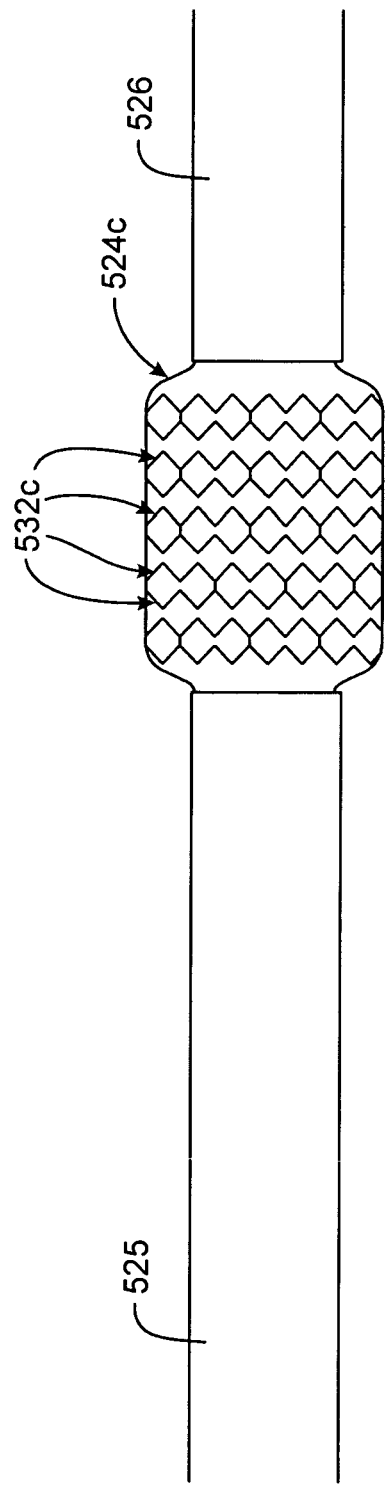

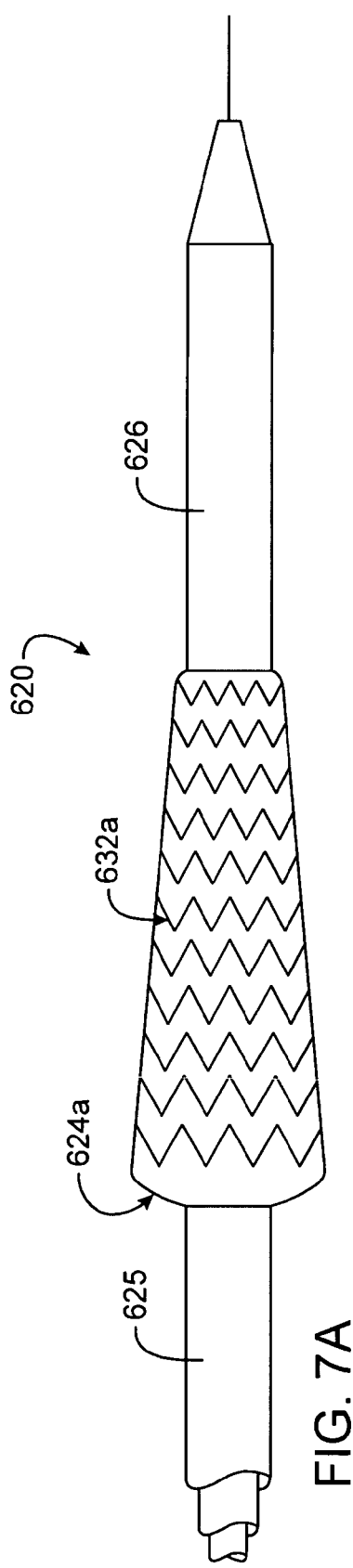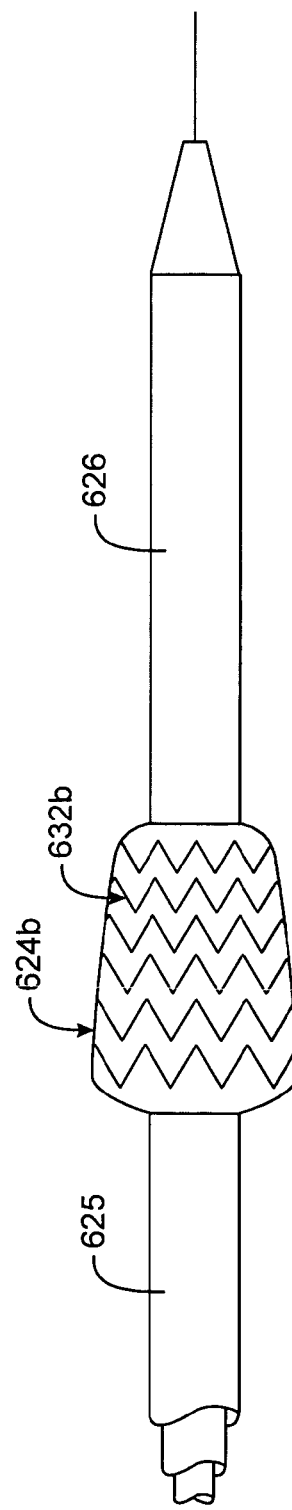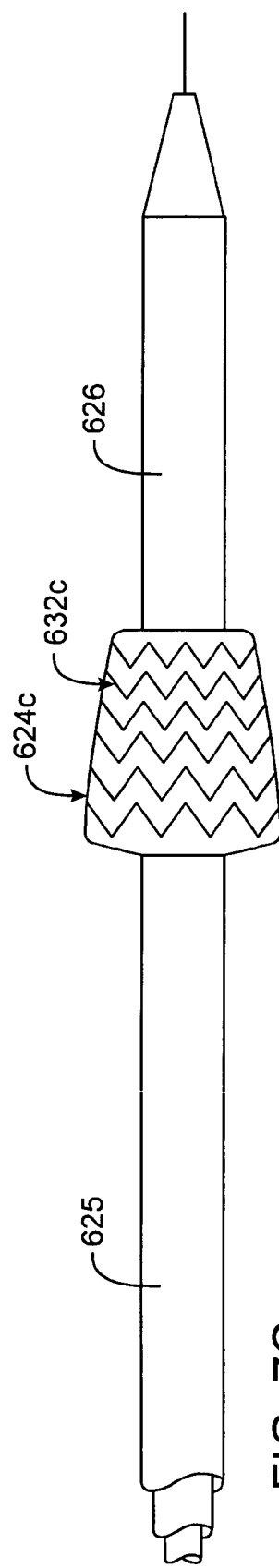

FIXED STENT DELIVERY DEVICES AND METHODS

BACKGROUND OF THE INVENTION

1. Field of the Invention

The present invention relates generally to medical devices and methods. More particularly, the invention relates to apparatus and methods for independently delivering a plurality of stents or stent segments within a body lumen.

Stenting has become an increasingly important treatment option for patients with coronary artery disease. Stenting involves the placement of a tubular prosthesis within a diseased coronary artery to expand the arterial lumen and maintain the patency of the artery. Early stent technology suffered from problems with restenosis, the tendency of the coronary artery to become re-occluded following stent placement. In recent years, however, improvements in stent design and the advent of drug-eluting stents have reduced restenosis rates dramatically. As a result, the number of stenting procedures being performed in the United States, Europe, and elsewhere has soared.

Stents are delivered to the coronary arteries using long, flexible vascular catheters, typically inserted through a femoral artery. For self-expanding stents, the stent is simply released from the delivery catheter, and it resiliently expands into engagement with the vessel wall. For balloon expandable stents, a balloon on the delivery catheter is expanded which expands and deforms the stent to the desired diameter, whereupon the balloon is deflated and removed.

Despite many recent advances in stent delivery technology, a number of shortcomings still exist. For example, current stent delivery catheters are not capable of customizing the length of the stent in situ to match the size of the lesion to be treated. While lesion size may be measured prior to stenting, using angiography or fluoroscopy, such measurements may be inexact. If a stent is introduced that is found to be of inappropriate size, the delivery catheter and stent must be removed from the patient and replaced with a different device of correct size. Moreover, current stent delivery devices cannot treat multiple lesions with a single catheter. If multiple lesions are to be treated, a new catheter and stent must be introduced for each lesion to be treated.

Additionally, currently available stent delivery devices are not well-adapted for treating vascular lesions that are very long and/or in curved regions of a vessel. Current stents have a discrete length that is relatively short due to their stiffness. If such stents were made longer, to treat longer lesions, they would not conform well to the curvature of vessels or to the movement of vessels on the surface of the beating heart. On the other hand, any attempt to place multiple stents end-to-end in longer lesions is hampered by the inability to maintain appropriate inter-stent spacing and to prevent overlap of adjacent stents. Such shortcomings in the prior art are addressed by the inventions described in U.S. patent application Ser. No. 10/412,714, entitled "Apparatus and Methods for Delivery of Multiple Distributed Stents," filed on Apr. 10, 2003; and U.S. patent application Ser. No. 10/637,713, entitled "Apparatus and Methods for Delivery of Multiple Distributed Stents," filed on Aug. 8, 2003; both applications assigned to the assignee of the present invention, and both applications being hereby incorporated fully by reference.

Even with improvements such as those described in the above-referenced patent applications, further improvements in stent delivery devices and methods are still being sought. For example, it may often be advantageous to have stents or stent segments mounted to an expandable deployment member, such as a balloon, at fixed positions along the balloon rather than being slidable along the balloon. This would lock in the relative positions of the stent segments to avoid overlap, excessive spacing, rotational misalignment during deployment, possible damage to the balloon or stent coatings and the like. Stent segments fixed to a balloon would also eliminate the need for a stent pusher to advance the stent segments distally, thereby reducing the profile, stiffness and complexity of the stent delivery catheter. Although conventional stenting devices have a stent pre-mounted to a balloon, currently available fixed-stent deployment devices typically only allow a single stent of fixed length to be deployed at once. It may be desirable, however, to tailor the length of the stent to match the size of the lesion being treated. It may also be desirable to deploy additional stents in one or more subsequent deployments without removing the catheter from the body. It may also be useful to deploy different sizes or types of stents during the same intervention, use different portions of an expandable member having different sizes or shapes, or select other characteristics of each stent deployed in the same intervention. These options are not provided by currently available pre-mounted stent delivery devices.

Therefore, a need exists for improved stent delivery devices and methods. Ideally, such devices and methods would reduce or eliminate the need for sliding stents along an expandable member such as a balloon. Also ideally, such devices and methods would allow for selective deployment of one or more stent segments of a stent. Such devices and methods should also allow in situ customization of stent size, shape, length, material, coating, and other characteristics to match the lesion being treated. Such devices and methods would also ideally be more easily manufactured and used than sliding-stent delivery devices. At least some of these objectives will be met by the present invention.

2. Description of the Background Art

U.S. patent application Ser. Nos. 10/412,714 and 10/637,713, previously incorporated by reference, describe apparatus and methods for delivery of multiple distributed stents. U.S. Pat. Nos. 6,485,510 and 6,258,117 to Camrud et al. describe segmented stents with breakable connections between the segments. U.S. Patent Application Publication No. 2002/0156496 (inventor Chermoni) describes a catheter for carrying stents including a stent positioner. U.S. Pat. No. 6,143,016 to Bleam et al. describes a stent delivery sheath. U.S. Pat. No. 5,807,398 to Shaknovich describes a shuttle stent delivery catheter. U.S. Pat. No. 5,571,036 (Kaplan et al.) and U.S. Pat No. 5,776,141 (Klein et al.) describe an expandable sleeve for placement over a balloon catheter for the delivery of one or two stent structures to the vasculature. U.S. Pat. No. 5,697,948 to Marin et al. describes a catheter for delivering stems covered by a sheath. Patent application Ser. Nos. 2003/0139797 (Johnson) and 2003/0114919 (McQuiston) describe covered segmented stents.

BRIEF SUMMARY OF THE INVENTION

Devices and methods of the present invention provide for delivering multiple stents or stent segments into a body lumen, such as a blood vessel. Typically, devices include a catheter having an expandable member with multiple stent segments mounted at fixed positions thereon. By "fixed positions," it is meant that the stent segments are not axially slidable, or are slidable only a limited distance, along the expandable member. In alternative embodiments, self-expanding stent segments may be used without an expandable member.

Stent segments are deployed from the catheter by moving at least one sheath overlying the expandable member to allow selected length(s) of the balloon to expand, thus permitting one or more individual stent segments or one or more groups of stent segments to be deployed at one time. In some embodiments, two sheaths are used or the expandable balloon is retracted within the catheter to allow for multiple inflations and deflations of the balloon to deploy subsequent stent segments. By mounting stent segments to an expandable member at fixed positions, sliding advancement of stents along the member is avoided, thus enhancing accuracy and efficiency of stent deployment and preventing damage to the balloon or stent coatings.

In one aspect of the present invention, a stent delivery device for delivering a plurality of stent segments to a treatment site includes: a catheter shaft having a proximal end and a distal end; an expandable member coupled with the catheter shaft near the distal end; a plurality of stent segments mounted on the expandable member; and at least a first axially movable sheath disposed over at least part of the catheter shaft, the expandable member and the stent segments. The first sheath is adapted to constrain expansion of a first portion of the expandable member and stent segments thereon while allowing expansion of a second portion of the expandable member and stent segments thereon. In some embodiments, each of the plurality of stent segments is spaced apart from adjacent stent segments, so that each stent segment can be expanded by the expandable member without interfering with adjacent stent segments.

Some embodiments further include at least a second axially movable sheath disposed over part of the catheter shaft, the expandable member and the stent segments. In such embodiments, the first sheath is disposed proximally along the catheter shaft relative to the second sheath, and the first and second sheaths are adapted to allow expansion and deployment of at least one stent segment between the sheaths. In some embodiments, for example, the second sheath may be movable distally to allow for deployment of at least one stent segment and proximally to constrain a portion of the expandable member from which at least one stent segment has been deployed. For example, the first sheath may be retracted to allow deployment of one or more stent segments, the second sheath may then be retracted to constrain the portion of the expandable member from which the first stent segments were deployed, the first sheath may be retracted to deploy one or more additional segments, and so on.

As an alternative to a second sheath, in one embodiment the stent delivery device includes an inner shaft slidably disposed within the catheter shaft. In this embodiment, the expandable member has a distal end coupled with the inner shaft for retracting relative to the catheter shaft a portion of the expandable member from which at least one stent segment has been deployed. Thus, as stent segments are deployed, the portion of the balloon from which they have been deployed is retracted within the catheter body.

In another aspect of the invention, a stent delivery device for delivering a plurality of stent segments to a treatment site comprises: a catheter shaft having a proximal end and a distal end; an expandable member coupled with the catheter shaft near the distal end; a plurality of stent segments mounted on the expandable member; at least one axially movable sheath disposed over at least part of the catheter shaft, the expandable member and the stent segments, wherein the sheath is adapted to constrain expansion of a first portion of the expandable member and stent segments thereon while allowing expansion of a second portion of the expandable member and stent segments thereon; and an inner shaft slidably disposed within the catheter shaft. In this embodiment, as just described, the expandable member includes a distal end coupled with the inner shaft for retracting relative to the catheter shaft a portion of the expandable member from which at least one stent segment has been deployed.

In another aspect of the invention, an interventional catheter device includes: a catheter shaft having a proximal end and a distal end; an expandable member coupled with the catheter shaft near the distal end; a distal sheath axially movable relative to the expandable member and positionable over at least a distal portion thereof; and a proximal sheath axially movable relative to the expandable member and the distal sheath and positionable over at least a proximal portion of the expandable member. The distal and proximal sheaths are axially positionable to expose a selected portion of the expandable member to allow expansion thereof while covering another portion of the expandable member to constrain expansion thereof.

Some embodiments also include a plurality of stents mounted on the expandable member. In such embodiments, the distal sheath may optionally be movable distally to allow for deployment of at least one stent and proximally to constrain a portion of the expandable member from which at least one stent has been deployed. Optionally, at least a first of the stents may have a different characteristic than at least a second of the stents, with the first and second stent segments being mounted at different locations along the expandable member. For example, the different stent segments may have different diameters, shapes, lengths, geometries, thicknesses, stiffness, stent materials, coating materials and/or the like.

In some embodiments, the expandable member may be tapered along its length, with the distal and proximal sheaths being positionable to expose at least a first portion of the expandable member having a first average cross-sectional diameter while covering at least a second portion of the expandable member having a second average cross-sectional diameter. In some embodiments, each of the plurality of stents may comprise a plurality of stent segments. Optionally, the length of each stent may be selected by selecting the number of stent segments. In alternative embodiments, the expandable member may include a first tapered portion having a first average cross-sectional diameter and a second tapered portion having a second average cross-sectional diameter, with the distal and proximal sheaths being positionable to expose the first portion while covering the second portion.

In yet another aspect of the present invention, a stent delivery device for delivering a plurality of stent segments to a treatment site comprises: a catheter shaft having a proximal end and a distal end; a plurality of self-expanding stent segments disposed on the catheter shaft; a distal sheath axially movable relative to the stent segments and positionable over at least one distal segment; and a proximal sheath axially movable relative to the stent segments and the distal sheath and positionable over at least one proximal segment. Here, the distal and proximal sheaths are axially positionable to expose one or more selected stent segments to allow expansion thereof while covering one or more other stent segments to constrain expansion thereof.

In another aspect of the invention, a method for delivering a plurality of stent segments to a treatment site includes: positioning a distal portion of a stent delivery catheter device at the treatment site; moving at least a first sheath of the catheter device to expose at least part of an expandable member on the catheter device and at least one of a plurality of stent segments mounted on the expandable member; and expanding the expandable member to deploy at least one of the plurality of stent segments at the treatment site. Optionally, the method may further involve moving the first sheath again to further expose the expandable member to deploy at least one additional stent segment, moving the first sheath a third time to further expose the expandable member to deploy at least one additional stent segment, and so on. In some embodiments, the additional stent segment(s) has a length different than the at least one stent segment.

In some embodiments, the method further involves restraining a first portion of the expandable member from which at least one stent segment has been deployed while expanding a second portion of the expandable member to deploy at least one additional stent segment. In some embodiments, restraining the first portion of the expandable member comprises moving a second sheath of the catheter device over the first portion of the expandable member from which at least one stent segment has been deployed. Alternatively, restraining the first portion of the expandable member may involve retracting a portion of the expandable member from which at least one stent segment has been deployed within the catheter device.

In another aspect of the present invention, a method for delivering a plurality of stent segments to treatment sites in a body lumen involves: positioning a distal portion of a stent delivery catheter device in the body lumen, the delivery catheter having a plurality of stent segments mounted thereon; moving at least a first sheath of the catheter device to deploy a first selected number of stent segments at a first treatment site; and moving at least the first sheath to deploy a second selected number of stent segments at a second treatment site, wherein the first selected number is different than the second selected number.

Optionally, such a method may further involve expanding a first portion of an expandable member of the stent delivery device to deploy the first selected number of stent segments and expanding a second portion of the expandable member to deploy the second selected number of stent segments. In some embodiments, the method may also include moving a second sheath to constrain the first portion of the expandable member before expanding the second portion of the expandable member. In alternative embodiments, the stent segments may be self-expanding so that moving the first sheath exposes the self-expanding stents to allow them to expand and deploy. Such methods may further include moving a second sheath to selectively deploy the second selected number of stent segments. In some embodiments, the first selected number of stents have a first expanded diameter, and the second selected number of stents have a second expanded diameter different than the first expanded diameter. In other embodiments, the first selected number of stents have a first geometry, and the second selected number of stents have a second geometry different than the first geometry.

Further aspects of the nature and advantages of the invention will become apparent from the detailed description below, in conjunction with the drawings.

BRIEF DESCRIPTION OF THE DRAWINGS

FIGS. 3A-3F are perspective-view diagrams of a distal portion of a stent delivery catheter, demonstrating a method for delivering multiple stent segments according to one embodiment of the invention.

FIGS. 5A and 5B are perspective views of a distal end of a stent delivery catheter having two sheaths, demonstrating how stents of different lengths may be deployed according to one embodiment of the invention.

FIGS. 6A-6C are perspective views of a distal end of a stent delivery catheter having two sheaths, demonstrating how differently configured stents may be deployed according to one embodiment of the invention.

FIGS. 7A-7C are perspective views of a distal end of a stent delivery catheter having two sheaths, demonstrating how different stent may be deployed using different portions of a tapered expandable member according to one embodiment of the invention.

DETAILED DESCRIPTION OF THE INVENTION

Figure 1:
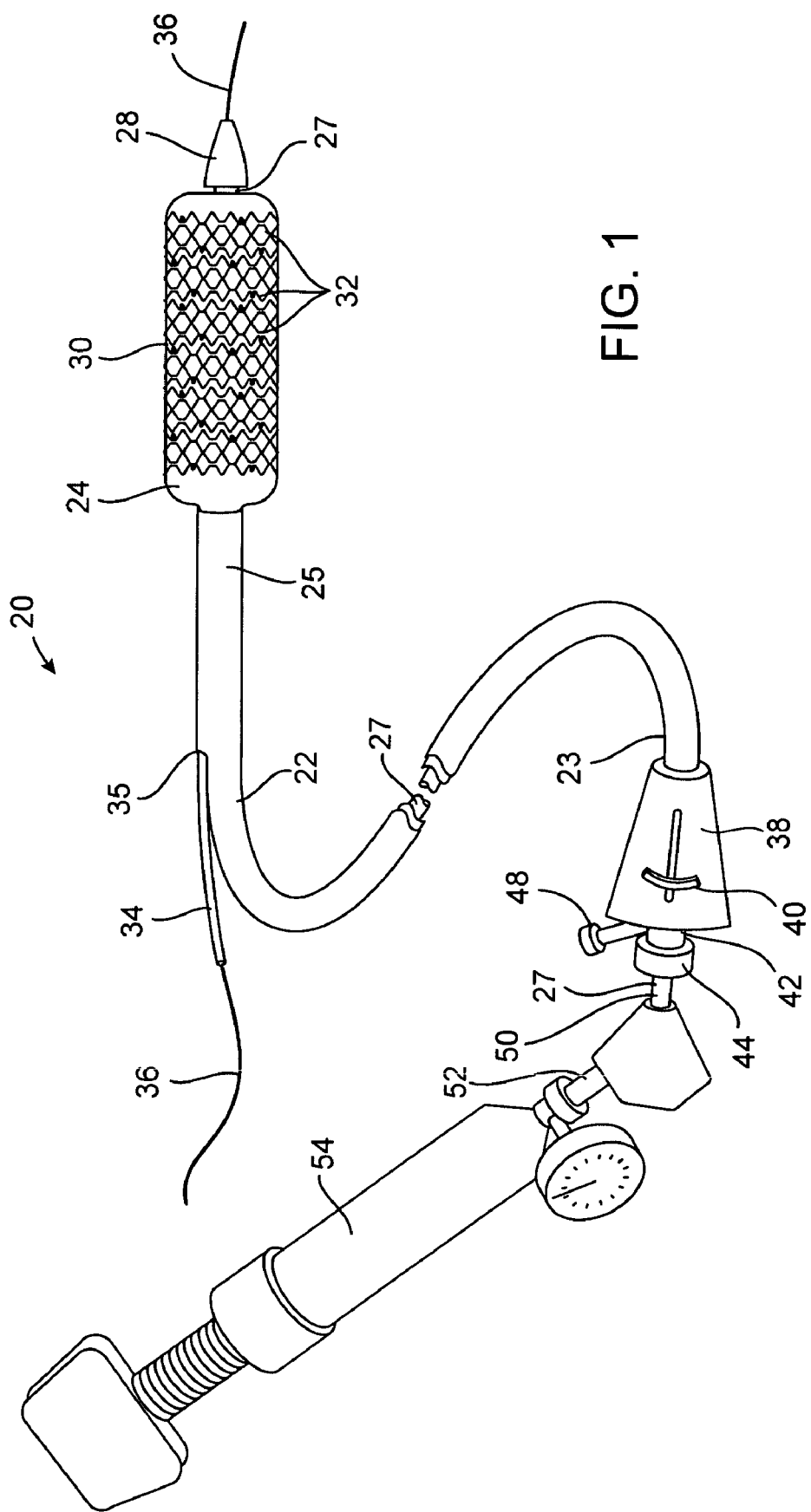
FIG. 1 is a perspective view of a stent delivery catheter according to one embodiment of the invention, with a sheath retracted and an expandable member inflated.

A first embodiment of a stent delivery catheter according to present invention is illustrated in FIG. 1. Stent delivery catheter 20 includes a catheter body 22 comprising an outer sheath 25 slidably disposed over an inner shaft 27. An expandable member 24, such as an inflatable balloon (shown in an inflated configuration), is mounted to inner shaft 27 and is exposed by retracting sheath 25 relative to inner shaft 27. A tapered nosecone 28, composed of a soft elastomeric material to reduce trauma to the vessel during advancement of the device, is mounted distally of expandable member 38. One or more stents 30, which preferably comprise a plurality of separate or separable stent segments 32, are mounted at fixed positions on expandable member 24 for expansion therewith. A guidewire tube 34 is slidably positioned through a guidewire tube exit port 35 in sheath 25 proximal to expandable member 24. A guidewire 36 is positioned slidably through guidewire tube 34, expandable member 24, and nosecone 28 and extends distally thereof.

A handle 38 is mounted to a proximal end 23 of sheath 25 and includes an actuator 40 slidably mounted thereto for purposes described below. An adaptor 42 is mounted to the proximal end of handle 38 and provides a catheter port 44 through which inner shaft 27 is slidably positioned. A flush port 48 is mounted to the side of adaptor 42 through which a fluid such as saline can be introduced into the interior of catheter body 22. An annular seal (not shown) in catheter port 44 seals around inner shaft 27 to prevent fluid from leaking through catheter port 44. Optionally, a clamp (not shown) such as a threaded collar, can be mounted to catheter port 44 to lock inner shaft 27 relative to handle 38.

Inner shaft 27 has a proximal end 50 to which is mounted an inflation adaptor 52. Inflation adaptor 52 is configured to be fluidly coupled to an inflation device 54, which may be any commercially available balloon inflation device such as those sold under the trade name "Indeflator™," available from Advanced Cardiovascular Systems of Santa Clara, Calif. Inflation adaptor 52 is in fluid communication with expandable member 24 via an inflation lumen (described below) in inner shaft 27 to enable inflation of expandable member 24.

Figure 2:
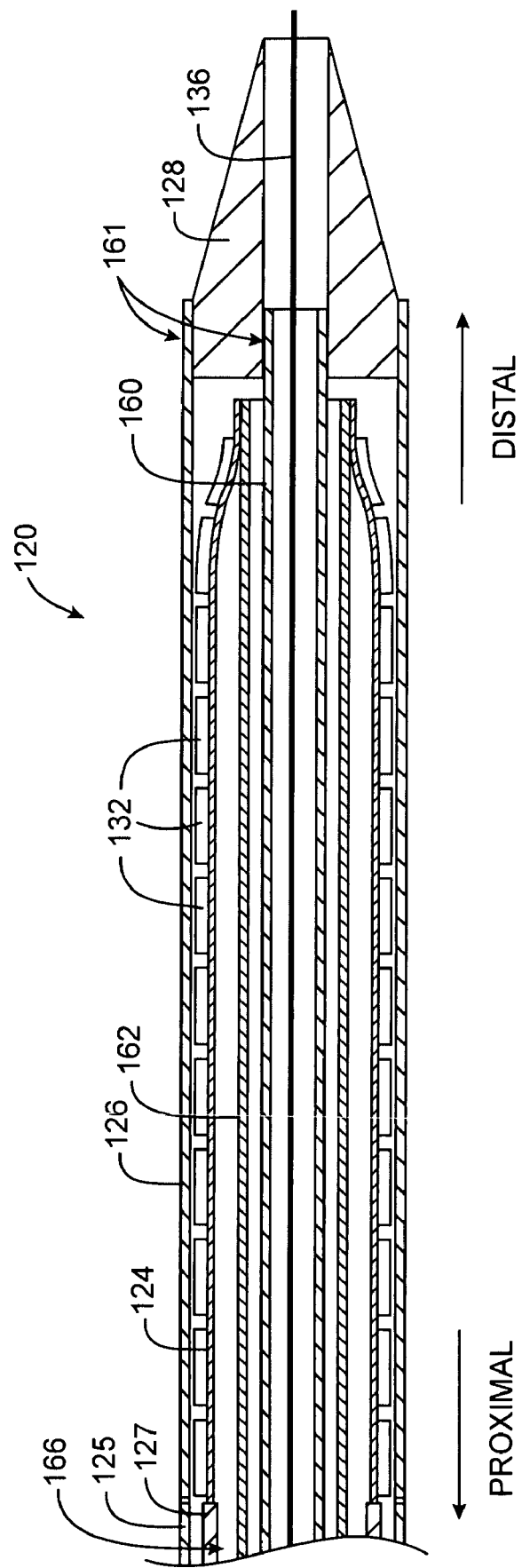
FIG. 2 is a side cross-section of a distal portion of a stent delivery catheter according to one embodiment of the present invention.

FIG. 1 shows an embodiment of a catheter device having one sheath. In alternative embodiments, two or more sheaths may be used. For example, and with reference now to FIG. 2, in one embodiment a distal portion of a stent delivery catheter 120 may suitably include a distal sheath 126, a proximal sheath 125, an outer expandable member shaft 127, an inner expandable member shaft 162, an expandable member 124, a distal sheath actuator 160 and a nosecone 128. Multiple stent segments 132 may be disposed along expandable member 124, and catheter 120 may be slidably disposed over a guidewire 136. Of course, many other configurations and combinations are encompassed within the scope of the present invention as it is defined in the appended claims. For example, in some embodiments, only one sheath is included. Other embodiments may include modifications or additional features, such as those described in U.S. patent application Ser. Nos. 10/412,714 and 10/637,713, which were previously incorporated by reference. Thus, stent delivery catheter 120 in FIG. 2 is but one exemplary embodiment.

That being said, proximal sheath 125 and distal sheath 126 are slidably disposed over expandable member 124 (and stent segments 132 disposed thereon) when in an unexpanded configuration. Distal sheath 126 is coupled with nosecone 128, and nosecone 128 is coupled with distal sheath actuator 160 at attachment points 161 via any suitable mechanism, such as adhesives, welding, press fitting or the like. These connections allow distal sheath actuator 160 to be used to axially move distal sheath 126 and nosecone 128 relative to the rest of catheter 120. For example, as will be explained in more detail below, distal sheath 126 may be moved distally to expose a portion of expandable member 124 and one or more stent segments 132 disposed thereon. Distal sheath 126 may also be positioned over expandable member 124 to constrain a portion of expandable member 124 from which one or more stent segments 132 have been deployed. Proximal sheath 125 typically extends up to the proximal end of distal sheath 126 from the proximal end (or nearly the proximal end) of catheter 120. Like distal sheath 126, proximal sheath 125 is also slidably disposed over expandable member 124. In various embodiments, proximal sheath 125 may be movable proximally, distally or both. For example, proximal sheath may sometimes be retracted proximally to expose a portion of expandable member 124 and one or more stent segments 132 between the two sheaths, but in some embodiments may also be advanced distally to cover a selected portion of expandable member 124 and stent segments 132 thereon.

Both distal sheath 126 and proximal sheath may have any suitable shape, length, cross-sectional diameter, material thickness, and the like and may be made of any suitable material or combination of materials. In one embodiment, for example, distal sheath 126 may have a length sufficient to cover the entirety of expandable member 124, in one embodiment being between about 15 cm and about 35 cm. Proximal sheath l25 may have a length selected to extend over the entirety of expandable member 124 as well, in one embodiment being between about 100 cm and about 125 cm. Either sheath may be constructed of any of a variety of biocompatible materials, such as but not limited to a polymer such as PTFE, FEP, polyimide, or Pebax, may be reinforced with a metallic or polymeric braid to resist radial expansion of expandable member 124, and/or the like.

Inner expandable member shaft 162 and outer expandable member shaft 127 are coupled with expandable member 124 to form an inflation lumen 166 that is in communication with the interior of expandable member 124. Both inner shaft 162 and outer shaft 127 may be formed of any suitable material(s), such as but not limited to a polymer such as PTFE, FEP, polyimide, or Pebax, and may be reinforced with a metallic braid for added radial strength and kink resistance. In the proximal extremity of delivery catheter 120, inner shaft 127 may comprise a similar polymer or a metal such as stainless steel or Nitinol.

Expandable member 124 comprises an expandable balloon that is joined to inner expandable member shaft 162 and outer expandable member shaft 127. Expandable member 124 may be formed of a semi-compliant polymer such as Pebax or Nylon. Distal sheath actuator 160 passes through the interior of inner expandable member shaft 162 and is mounted to nosecone 128 at one of the attachment points 161, thereby providing a passage through catheter 20 through which guidewire 136 may pass.

Stent segments 132 are mounted at fixed positions along expandable member 124. In an exemplary embodiment, each stent segment is about 2-8 mm in length, and up to 10-50 stent segments may be positioned end-to-end in a line over expandable member 124. In some embodiments, stent segments 132 are mounted to expandable member 124 with an inter-segment spacing selected to allow expansion of one segment while an adjacent segment is constrained within one or both sheaths 125, 126. Alternatively, separate spacing elements may be disposed between adjacent stent segments 132, the spacing elements being fixed with stent segments 132 on expandable member 124. In some embodiments, such spacing elements may be plastically deformable or self-expanding so as to be deployable with stent segments 132 into the vessel. Alternatively, spacing elements may be configured to remain on expandable member 124 following stent deployment. For example, such spacing elements could comprise elastic rings which elastically expand with expandable member 124 and resiliently return to their unexpanded shape when expandable member 124 is deflated. In another alternative embodiment, expandable member 124 could have ridges, bumps or other surface features configured to maintain inter-segment spacing.

Stent segments 132 are preferably constructed of a malleable metal so as to be plastically deformable by expandable member 124 as they are expanded to the desired diameter in the vessel. Alternatively, stent segments 132 may be formed of an elastic or super elastic shape memory material such as Nitinol so as to self-expand upon release into the vessel by retraction of one or both sheaths 125, 126. Stent segments 132 may also be composed of polymers or other suitable biocompatible materials. In self-expanding embodiments, expandable member 124 may also be used for predilatation of a lesion prior to stent deployment or for augmenting the expansion of the self-expanding stent segments.

In some embodiments, stent segments 132 are coated, impregnated, infused or otherwise coupled with one or more drugs that inhibit restenosis, such as Rapamycin, Everolimus, Paclitaxel, analogs, prodrugs, or derivatives of Rapamycin, Everolimus or Paclitaxel, or other suitable agent(s), preferably carried in a bioerodable polymeric carrier. Alternatively, stent segments 132 may be coated with other types of drugs or therapeutic materials such as antibiotics, thrombolytics, antithrombotics, anti-inflammatories, cytotoxic agents, anti-proliferative agents, vasodilators, gene therapy agents, radioactive agents, immunosuppressants, chemotherapeutics and/or stem cells. Such materials may be coated over all or a portion of the surface of stent segments 132, or stent segments 132 may include apertures, holes, channels, or other features in which such materials may be deposited.

Stent segments 132 may have a variety of configurations, including those described in copending application Ser. No. 60/440,839, filed Jan. 17, 2003 which is hereby incorporated fully by reference, and Ser. No. 10/637,713, which was previously incorporated by reference. Stent segments 132 are preferably completely separate from one another without any interconnections, but alternatively may have couplings between two or more adjacent segments which permit flexion between the segments. As a further alternative, one or more adjacent stent segments 132 may be connected by separable or frangible couplings that are separated prior to or upon deployment, as described in copending application Ser. No. 10/306,813, filed Nov. 27, 2002, which is incorporated herein by reference.

With one or both sheaths 125, 126 retracted and/or advanced a desired distance, expandable member 124 is allowed to expand when inflation fluid is delivered through inflation lumen 166, thereby expanding a desired number of stent segments 132 exposed between proximal sheath 125 and distal sheath 126. The remaining portion of expandable member 124 and the remaining stent segments 132 within sheaths 125, 126 are constrained from expansion by sheaths 125, 126.

Figure 3A:
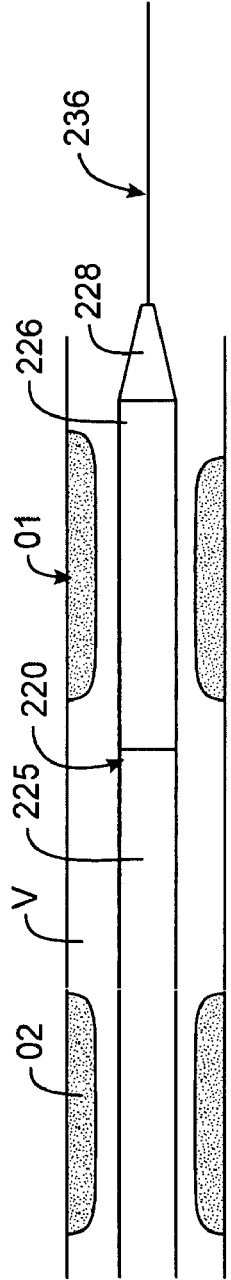

Referring now to FIGS. 3A through 3F, one embodiment of a method for using a stent delivery catheter 220 similar to the one shown in FIG. 2 is demonstrated in a series of diagrams. In FIG. 3A, catheter 220 is advanced to a location in a blood vessel V for treating a first occlusion O1 with one or more stents or stent segments. Catheter device 220 generally includes a distal sheath 226, a proximal sheath 225 and a nosecone 228 and is advancable over a guidewire 236.

Figure 3B:
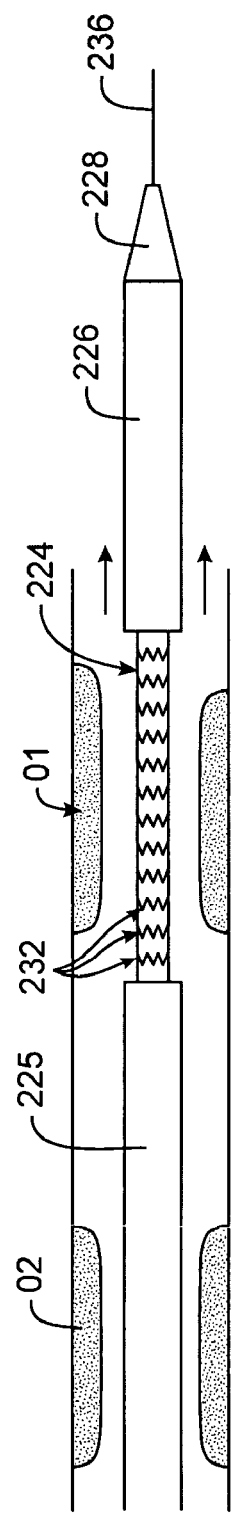
Figure 3C:
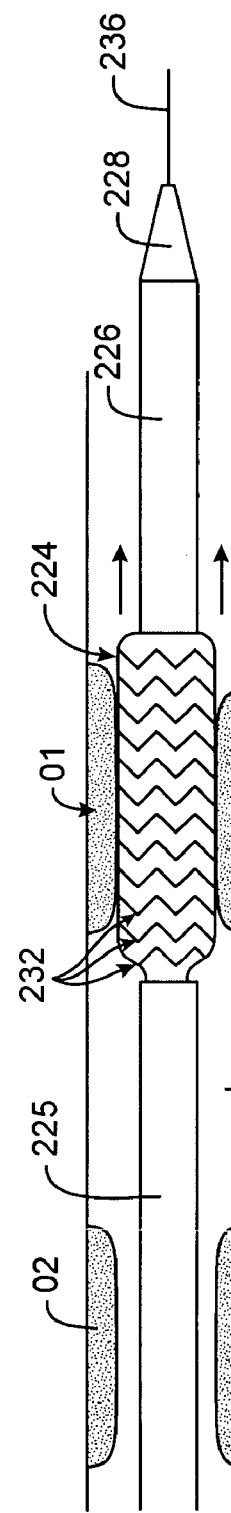
Figure 3D:
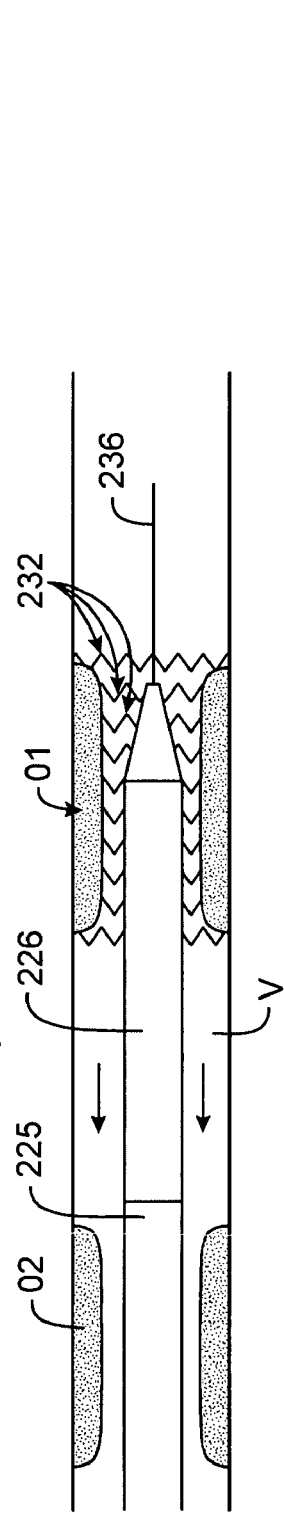

In FIG. 3B, distal sheath 226 is advanced distally (shown by horizontal arrows) to expose a portion of an expandable member 224 having length suitable for occlusion 01 and stent segments 232 disposed thereon. In an alternative embodiment of the method, catheter 220 may be positioned such that proximal sheath 225 may be retracted to expose the portion of expandable member 224 and corresponding stent segments 232. Next, as shown in FIG. 3C, expandable member 224 may he expanded to expand stent segments 232, to contact stent segments 232 with the first occlusion 01. Expandable member 224 may then be deflated (not shown), leaving stent segments in the vessel V. As shown in FIG. 3D, distal sheath 226 may then be retracted (horizontal arrows) to cover and constrain the portion of expandable member 224 from which stent segments 232 have been deployed.

As also shown in FIG. 3D, catheter 220 may next be repositioned in the vessel V for treatment of a second occlusion O2. Proximal sheath 225 may be retracted, as shown in FIG. 3E, to expose a more proximal portion of expandable member 224 having a desired length for occlusion O2, while distal sheath 226 constrains the portion from which stent segments 232 have been deployed. When expandable member 224 is expanded, as in FIG. 3F, the constraint by distal sheath 226 prevents the portion of expandable member 224 that no longer holds stents from expanding, which might disrupt already-placed stents, damage expandable member 224, damage the vessel V and/or the like. The exposed portion of expandable member 224 expands stent segments 232 mounted thereon in contact with the second occlusion O2. Again, expandable member 224 may be deflated, distal sheath 226 may be retracted, and additional stent segments 232 may be deployed. Alternatively, stent delivery catheter may be removed from the vessel V. Using methods and devices such as those just described enhances delivery of multiple stents or stent segments of various lengths to more than one occlusion, lesion, treatment site or the like.

Obviously, the above description is but one of a number of possible embodiments of methods for delivering stents or stent segments according to the invention. Steps may be modified, deleted or added, the order of steps may be changed, and/or the like, without departing from the scope of the invention. In some embodiments, for example, only one sheath is used. In such embodiments, all stent segments that are desired to be deployed may be deployed with one expansion of the expandable member, for example. In other embodiments using two sheaths, the way or order in which the sheaths are moved relative to one another and to other parts of the catheter device may be altered as desired. Therefore, the foregoing example is provided for exemplary purposes only and should not be interpreted to limit the scope of the present invention.

Figure 4:
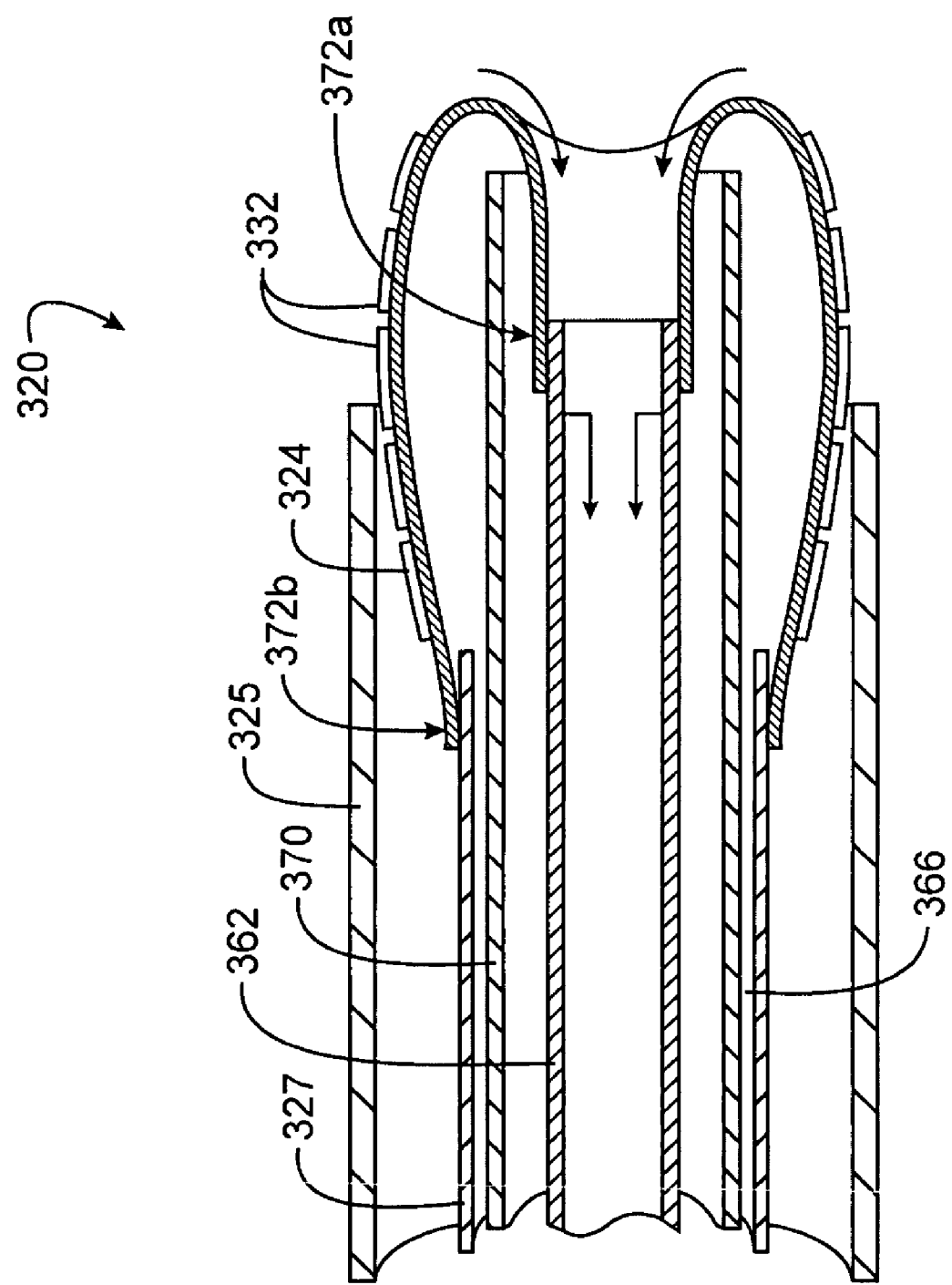
FIG. 4 is a side cross-section of a distal portion of a stent delivery catheter according to another embodiment of the present invention.

Referring now to FIG. 4, an alternative embodiment of a stent delivery catheter device 320 may also enhance serial stent deployment while protecting an expandable member 324 of the device. In this embodiment, the distal end of expandable member 324 is coupled to an inner balloon shaft 362 at a first attachment point 372a, and the proximal end of expandable member 324 is coupled to an outer balloon shaft 327 at a second attachment point 372b. Between inner shaft 362 and outer shaft 327 is an axial support shaft 370, and between axial support shaft 370 and outer shaft 327 is an inflation lumen 366. A sheath 325 is slidably disposed over balloon shaft 327, enabling the length of the expandable portion of the balloon to be changed. As stent segments 332 are deployed from the distal portion of expandable member 324, inner balloon shaft 362 may be retracted proximally within axial support shaft 370 (horizontal lines) to pull the distal portion of expandable member 324 within the axial support shaft 370 (curved arrows). Thus, multiple stents or stent segments 332 may be deployed at multiple locations, multiple lesions or the like by inflating and deflating expandable member 324 multiple times, while constraining the portion of expandable member 324 from which stent segments 332 have been deployed.

FIGS. 5A and 5B demonstrate one way in which a stent delivery catheter device 420 of the present invention may be used to deliver stents having different lengths and/or different numbers of stent segments 432. In FIG. 5A, a distal sheath 426 and a proximal sheath 425 are positioned to expose a first portion of an expandable member 424a and a stent having a first length. In FIG. 5B, distal sheath 426 and proximal sheath 425 are positioned to expose a second, shorter portion of expandable member 424b and a shorter stent. Of course, any number of different stents or stent segments may be mounted in fixed positions on expandable member 424 and proximal and distal sheaths 425, 426 may be positioned in any number of combinations to allow a physician to places various stents/segments at various locations to treat multiple lesions.

Referring now to FIGS. 6A-6C, embodiments of a stent delivery catheter device 520 may also be used to deliver multiple different types of stents having different characteristics within the same vessel or during the same procedure. For example, if stents having multiple different configurations are mounted at different fixed positions along an expandable member 524, a distal sheath 426 and a proximal sheath 425 may be positioned variously to allow expansion and deployment of the different stents at different locations. In FIG. 6A, for example, sheaths 425, 426 may be moved to expose a first portion of expandable member 524a to expose a first stent 532a having a zig-zag configuration. As in FIG. 6B, sheaths 425, 426 may be moved to expose a second portion of expandable member 524b, to deploy a second stent 432b with a "closed-cell" or honeycomb configuration. A third portion of expandable member 524c may then be exposed to deploy a third stent having multiple stent segments 532c. Again, any number of combinations of stents, stent positions and the like may be used. Stents having various lengths, diameters, strut thicknesses, geometries, materials, stiffness and coatings may be mounted at different locations along the expandable member allowing the user to select the ideal stent for each lesion treated.

With reference now to FIGS. 7A-7C, one embodiment of a stent delivery catheter device 620 may include a tapered expandable member 624 having a decreasing cross-sectional diameter from its proximal end to its distal end. Such tapered expandable members are disclosed in co-pending U.S. patent application Ser. No. 10/458,062, the full disclosure of which is hereby incorporated by reference. Using a distal sheath 626 and a proximal sheath 625, the entire expandable member 624 may be exposed or portions may be selectively exposed to allow expansion and delivery of a selected number of stents or stent segments 632 to a selected diameter or taper. In FIG. 7A, for example, a long portion of expandable member 624a is exposed to allow deployment of a first number of stent segments 632a. In FIG. 7B, a shorter portion of expandable member 624b is exposed to deploy a different selected number of stent segments 632b, the exposed portion being closer to the proximal end of expandable member 624 than the distal end and having a relatively larger expanded diameter. In FIG. 7C, a different portion of expandable member 624c is exposed to allow deployment of yet another set of stent segments 632c having a smaller expanded diameter. Using such an embodiment allows a physician to choose different portions of a tapered expandable member 624 for deploying stent segments 632, each portion having a different expanded diameter. This may be advantageous, for example, in placing multiple stents or stent segments in a tapered blood vessel or a vessel having varying diameters along its length at a treatment site. Further, the taper angle of the expandable member may be different at different axial locations on the expandable member, allowing the physician to select the ideal taper for the vessel being treated.

The above-described concepts of utilizing a tapered balloon having either constant or various taper angles with one or more sheaths to select a desired taper can also be applied to dilatation catheters for performing balloon angioplasty. Such catheters may be utilized in a manner similar to that shown in FIGS. 7A-7C, without the use of stents or stent segments on the expandable member. Moreover, a combination dilatation/stenting catheter is also within the scope of the invention, wherein a first portion of the balloon (usually near the distal end) has no stents disposed around it and is configured for dilatation, while a second portion of the balloon has stents positioned over it for expansion. In this way, the first portion of the balloon may be exposed for dilatation of a lesion while the second portion is covered by a sheath. Following dilatation, the first portion may be covered by a sheath while the second portion is expanded to deploy the stents in the lesion. Advantageously, the lengths of both the first and second portion may be adjusted so as to tailor the dilatation balloon and the stent to the size of the lesion treated.

Although the above is complete description of the preferred embodiments of the invention, various alternatives, additions, modifications and improvements may be made without departing from the scope thereof, which is defined by the claims.

What is claimed is:

1. method for delivering a plurality of stent segments to a treatment site, the method comprising:
   positioning a distal portion of a stent delivery catheter device at the treatment site;
   axially moving a first sheath and a second sheath of the catheter device to expose at least part of a radially expandable member on the catheter device and at least one of a plurality of separately deployable stent segments mounted on the expandable member; and
   radially expanding only the exposed part of the expandable member to deploy the one stent segment at the treatment site while a second portion of the expandable member and at least one remaining stent segment of the plurality remains unexpanded on the delivery device unconnected with the one stent segment and the at least one remaining stent segment is constrained by either the first sheath or the second sheath after the one stent segment has been fully deployed.

2. A method as in claim 1, further comprising moving the first sheath again to further expose the expandable member to deploy at least one additional stent segment.

3. A method as in claim 2, wherein the at least one additional stent segment has a length different than the at least one stent segment.

4. A method as in claim 1, further comprising restraining a first portion of the expandable member from which at least one stent segment has been deployed while expanding a second portion of the expandable member to deploy at least one additional stent segment.

5. A method as in claim 4, wherein restraining the first portion of the expandable member comprises moving a second sheath of the catheter device over the first portion of the expandable member from which at least one stent segment has been deployed.

6. A method as in claim 4, wherein restraining the first portion of the expandable member comprises retracting a portion of the expandable member from which at least one stent segment has been deployed within the catheter device.

7. A method for delivering a plurality of stent segments to treatment sites in a body lumen of a patient, the method comprising:
   positioning a distal portion of a stent delivery catheter device in the body lumen, the delivery catheter having a first sheath, a second sheath adjacent the first sheath, an expandable member and a plurality of stent segments mounted thereon, the stent segments and expandable member being at least partially covered by the first and second sheath;
   moving at least one of the first sheath or the second sheath of the catheter device to expose a first portion of the expandable member so as to allow deployment of a first selected number of stent segments at a first treatment site while a second portion of the expandable member and at least one remaining stent segment remains constrained by either the first or the second sheath after the first selected number of stent segments have been fully deployed, and the wherein the at least one remaining stent segment is unconnected with the first selected number of stent segments after deployment thereof;
   repositioning the delivery catheter to a second treatment site in the body lumen spaced apart from the first treatment site without removing the delivery catheter from the patient; and
   moving at least one of the first sheath or the second sheath to deploy a second selected number of stent segments at the second treatment site, wherein the first selected number is different than and unconnected to the second selected number.

8. A method as in claim 7, further comprising:
   expanding a first portion of an expandable member of the stent delivery device to deploy the first selected number of stent segments; and
   expanding a second portion of the expandable member to deploy the second selected number of stent segments.

9. A method as in claim 8, further comprising moving a second sheath to constrain the first portion of the expandable member before expanding the second portion of the expandable member.

10. A method as in claim 7, wherein the stent segments are self-expanding so that moving the first sheath exposes the self-expanding stents to allow them to expand and deploy.

11. A method as in claim 10, further including moving a second sheath to selectively deploy the second selected number of stent segments.

12. A method as in claim 7, wherein the first selected number of stents have a first expanded diameter, and the second selected number of stents have a second expanded diameter different than the first expanded diameter.

13. A method as in claim 7, wherein the first selected number of stents have a first geometry, and the second selected number of stents have a second geometry different than the first geometry.

* * * * *